(12) United States Patent
Tulchinsky et al.

(10) Patent No.: US 8,394,978 B2
(45) Date of Patent: Mar. 12, 2013

(54) SULFONATED ORGANOPHOSPHINE COMPOUNDS AND USE THEREOF IN HYDROFORMYLATION PROCESSES

(75) Inventors: Michael L. Tulchinsky, Midland, MI (US); Anthony G. Abatjoglou, Charleston, WV (US)

(73) Assignee: Dow Global Technologies LLC, Midland, MI (US)

( * ) Notice: Subject to any disclaimer, the term of this patent is extended or adjusted under 35 U.S.C. 154(b) by 208 days.

(21) Appl. No.: 12/812,985

(22) PCT Filed: Jan. 9, 2009

(86) PCT No.: PCT/US2009/030560
§ 371 (c)(1),
(2), (4) Date: Aug. 2, 2010

(87) PCT Pub. No.: WO2009/091671
PCT Pub. Date: Jul. 23, 2009

(65) Prior Publication Data
US 2011/0054205 A1     Mar. 3, 2011

Related U.S. Application Data

(60) Provisional application No. 61/021,070, filed on Jan. 15, 2008.

(51) Int. Cl.
*C07F 15/00*    (2006.01)
(52) U.S. Cl. .................. 556/21; 568/420; 568/454
(58) Field of Classification Search ............ 556/21; 568/420, 454
See application file for complete search history.

(56) References Cited

U.S. PATENT DOCUMENTS

| | | | |
|---|---|---|---|
| 2,900,393 A | 8/1959 | Broderick | |
| 3,527,809 A | 9/1970 | Pruett et al. | |
| 4,148,830 A | 4/1979 | Pruett et al. | |
| 4,247,486 A | 1/1981 | Brewester et al. | |
| 4,283,304 A | 8/1981 | Bryant et al. | |
| 4,483,802 A | 11/1984 | Gartner et al. | |
| 4,625,068 A | 11/1986 | Young | |
| 4,642,388 A | 2/1987 | Young | |
| 4,689,437 A * | 8/1987 | Murray ............ | 585/526 |
| 4,716,138 A | 12/1987 | Murray | |
| 4,731,486 A * | 3/1988 | Abatjoglou et al. ...... | 568/454 |
| 4,822,915 A | 4/1989 | Murray | |
| 5,180,854 A | 1/1993 | Abatjoglou et al. | |
| 5,382,701 A | 1/1995 | Suciu et al. | |
| 5,451,698 A | 9/1995 | Bahrmann et al. | |
| 5,663,426 A | 9/1997 | Albanese et al. | |
| 5,728,886 A | 3/1998 | Naumann et al. | |
| 5,760,286 A | 6/1998 | Brandvold | |
| 5,773,666 A | 6/1998 | Omatsu et al. | |
| 5,780,674 A | 7/1998 | Albanese et al. | |
| 5,925,785 A | 7/1999 | Stelzer et al. | |
| 5,929,289 A | 7/1999 | Abatjoglou et al. | |
| 5,932,772 A | 8/1999 | Argyropoulos et al. | |
| 5,952,530 A | 9/1999 | Argyropoulos et al. | |
| 6,103,908 A | 8/2000 | Bahrmann et al. | |
| 6,339,174 B1 | 1/2002 | Bogdanovic | |
| 6,610,881 B1 | 8/2003 | Riedel et al. | |
| 6,613,939 B2 | 9/2003 | Aouni et al. | |
| 6,864,387 B2 | 3/2005 | Riedel et al. | |
| 7,615,658 B2 * | 11/2009 | Lysenko et al. ............ | 554/143 |
| 7,663,002 B2 * | 2/2010 | Peng et al. ............ | 568/454 |
| 2003/0204109 A1 | 10/2003 | Aouni et al. | |
| 2009/0253907 A1 * | 10/2009 | Plenio et al. ............ | 544/163 |

FOREIGN PATENT DOCUMENTS

| | | |
|---|---|---|
| EP | 0350921 A1 | 1/1990 |
| EP | 1620387 A2 | 2/2006 |
| WO | WO-2004/094440 A2 | 11/2004 |
| WO | WO-2004/096744 | 11/2004 |
| WO | WO-2007035540 A2 | 3/2007 |

OTHER PUBLICATIONS

Abatjoglou et al, Organometallics, 1984, p. 923-926, vol. 3, American Chemical Society.
Arvidsson et al, Canadian Journal of Chemstry, 1998, p. 795-799, vol. 76, Canada.
Ashby, Journal of Organic Chemistry, 1985, p. 3274-3283, vol. 50, American Chemical Society.
Bartik et al, Journal of Molecular Catalysis A: Chemical, 1995, p. 117-122, vol. 98, Elsevier Science BV.
Bartik et al, Organometallics, 1993, p. 164-170, vol. 12, American Chemical Society.
Doppiu et al, European Journal of Inorganic Chemistry, 2004, p. 2244-2252, Wiley-VCH.
Fleckenstein et al, Chemistry—A European Journal, 2007, p. 2701-2716, vol. 13, Wiley-VCH.
Frohning, Applied Homogeneous Catalysis with Organometallic Compounds, 2002, p. 29-103, vol. 1, Wiley-VCH, New York.
Fürstner el al, Chemistry—A European Journal, 2000, p. 1847-1857, vol. 6, Wiley-VCH.
Jane et al, Journal of Organometallic Chemistry, 2000, p. 55-64, vol. 606, Elsevier Science SA.

(Continued)

*Primary Examiner* — Sudhakar Katakam
*Assistant Examiner* — Pancham Bakshi

(57) ABSTRACT

A compound comprising a sulfonated triorganophosphine of formula $R^1R^2PR^3[SO_3M]_n$, wherein $R^1$ and $R^2$ are selected individually from alkyl, aralkyl, and alicyclic groups; wherein $R^3$ represents a branched divalent or polyvalent, alkylene or alicyclic radical that is bonded to the phosphorus atom and to one or more sulfonate substituents, and further wherein $R^3$ does not contain any aryl moieties; M represents a monovalent cation; and n is an integer representing a total number of sulfonated substituents. The compound is useful as a ligand in transition metal-ligand complex catalysts that are capable of catalyzing the hydroformylation of an olefinically-unsaturated compound with carbon monoxide and hydrogen to form one or more corresponding aldehyde products. The ligand is incapable of alkyl-aryl exchange, thereby leading to reduced ligand usage and improving ligand and transition metal, e.g., rhodium, recovery and recycling, as compared with prior art ligands.

18 Claims, 3 Drawing Sheets

OTHER PUBLICATIONS

Kabalka et al, Tosylation of Alcohols, Journal of Organic Chemistry, 1986, p. 2386-2388, vol. 51, American Chemical Society.
Lynn et al, Journal of the American Chemical Society, 2000, p. 6601-6609, vol. 122, American Chemical Society.
Lysenko et al, Journal of Organometallic Chemistry, 2006, p. 5197-5203 vol. 69, Elsevier BV.
McNulty et al, Tetrahedron Letters, 2004, p. 407-409, vol. 45, Elsevier Ltd.
Mohr et al, Organometallics, 1996, p. 4317-4325, vol. 15, American Chemical Society.
Roman Jr. et al, Organometallics, 1997, p. 1484-1490, vol. 16, American Chemical Society.
Tugcu et al, Industrial and Engineering Chemical Research, 2002, p. 6482-6492, vol. 41, American Chemical Society.
Wyatt et al, European Journal of Organic Chemistry, 2003, p. 4216-4226, Wiley-VCH.
Yamamoto et al, Chemistry Letters, 1984, p. 1603-1606 ,vol. 7.
Yamamoto et al, Chemistry Letters, 1989, p. 349-352, vol. 1.
PCT/US09/030553 International Search Report.
PCT/US09/030553 Written Opinion of the International Search Authority.
PCT/US09/030553 International Preliminary Report on Patentability.

* cited by examiner

Synthetic Sequence for Ligand 1

Alternative Synthesis of Ligand 1 Intermediate

SULFONATED ORGANOPHOSPHINE COMPOUNDS AND USE THEREOF IN HYDROFORMYLATION PROCESSES

CROSS-REFERENCE TO RELATED APPLICATION

This application claims the benefit of U.S. Provisional Application Ser. No. 61/021,070, filed Jan. 15, 2008.

BACKGROUND OF THE INVENTION

This invention pertains to a novel class of sulfonated organophosphine compounds and their use as ligands in metal-ligand complex catalysts that are capable of catalyzing hydroformylation processes.

Hydroformylation processes are well known in the art, for example, as described in "Applied Homogeneous Catalysis with Organometallic Compounds," edited by B. Cornils and W. A. Herrmann, VCH, New York, 1996, vol. 1, pp. 29-104. Hydroformylation involves conversion of an olefinically-unsaturated reactant with carbon monoxide and hydrogen (syngas) to produce one or more corresponding formyl-substituted products (aldehydes). Hydroformylation processes are known to be catalyzed by metal-ligand complex catalysts, preferably, a transition metal-organophosphorus ligand complex catalyst. Representative art disclosing hydroformylation catalysts comprising a variety of triorganophosphine, triorganophosphite, diorganophosphite, and bisphosphite ligands is found in the following reference "Rhodium Catalyzed Hydroformylation," edited by P. W. N. M. van Leeuwen and C. Claver, Kluwer Academic Publisher, USA Edition, 2002. If desired, the formyl-substituted products can be subjected to downstream functionalization processes, for example, reduction of the aldehyde to form an alcohol; or reductive amination of the aldehyde to form an amine; or oxidation of the aldehyde to form a carboxylic acid; or aldolization of the aldehyde followed by oxidation to form an hydroxyacid. Alcohols, amines, carboxylic acids, and hydroxyacids obtained via hydroformylation of an olefinically-unsaturated reactant find utility as solvents, surfactants, and monomers for the preparation of polymers, and as intermediates in the synthesis of pharmaceuticals and other industrially-useful chemicals. Preferably, mono-, di-, and tri-alcohols and corresponding amines obtained directly from hydroformylation can be converted via transesterification into polyester polyols and polyester polyamines, respectively, which are especially useful in the manufacture of polyurethane polymers.

The hydroformylation of long-chain olefinically-unsaturated reactants having from about 6 to about 60 carbon atoms is of present day interest. In particular, one class of long-chain olefinically-unsaturated reactants comprises a mixture of mono-, di-, and tri-unsaturated fatty acids or fatty acid esters having from about 10 to about 50 carbon atoms, preferably, the olefinically-unsaturated fatty acid esters of lower alkanols, preferably, $C_{1-8}$ alkanols (mono-alkanols), for example, methanol. Olefinically-unsaturated fatty acid esters of the lower alkanols are themselves derived by transesterifying a seed oil, for example, a soy, castor, or canola vegetable oil, with the $C_{1-8}$ alkanol. Thus, seed oils can provide renewable alternative feedstocks of olefinically-unsaturated fatty acids or fatty esters, which are capable, in part, of replacing petroleum in the manufacture of industrially-useful chemicals.

More specifically, the present day hydroformylation of olefinically-unsaturated fatty acids or fatty esters and other long chain olefinically-unsaturated compounds is conducted in a rhodium-catalyzed one-phase process containing a water-soluble ionic ligand, preferably, an alkali metal salt of a dihydrocarbylarylphosphine monosulfonate compound wherein the hydrocarbyl comprises an alkyl or aryl group, and further containing a solubilizing solvent, such as N-methyl-2-pyrrolidinone (NMP), as disclosed for example in WO 2004/096744. Separation of the resulting aldehyde-containing reaction product fluid is advantageously effected by addition of water, as disclosed for example in U.S. Pat. No. 5,180,854, under conditions sufficient to obtain a non-polar phase containing one or more aldehyde products and optionally non-polar solvent(s) as may be present and a polar phase containing the rhodium-ligand catalyst, optional free ionically-charged ligand, water, and solubilizing solvent. Disadvantageously, ligands containing an aryl-phosphorus bond tend to undergo alkyl-aryl exchange by way of reaction of the phosphine ligand with the olefinically-unsaturated compound, as disclosed in U.S. Pat. No. 4,283,304 and by A. G. Abatjoglou, et al., in *Organometallics*, 1984, 3, 923-926.

Ligand alkyl-aryl exchange generates three undesirable results. First, alkyl-aryl exchange consumes the particular species of ligand active in the hydroformylation process, which then needs to be replaced. Second, alkyl-aryl exchange produces non-ionic or neutral ligands, which are insoluble in water and which can remain as free ligands or as coordinated ligands in rhodium complexes in the non-polar phase containing the aldehyde product(s), rather than being extracted into the polar phase. Third, alkyl-aryl exchange produces sodium benzenesulfonate, which accumulates in the polar phase and can eventually precipitate onto the walls of the reactor equipment and foul the same. Sodium benzenesulfonate may also induce undesirable separation of the water/NMP polar phase.

In view of the above, a search continues to discover novel compounds that can be utilized as ligands in transition metal-ligand complex catalysts for the hydroformylation of olefinically-unsaturated compounds, particularly, unsaturated fatty acids and fatty esters and other long-chain olefinically unsaturated compounds. It would be desirable for such novel compounds to provide for comparable or better olefin conversion and product selectivity as compared with prior art organophosphorus ligands. Moreover, it would be desirable for such novel compounds to provide for improved ligand stability with elimination of alkyl-aryl exchange, as compared with prior art ligands.

U.S. Pat. No. 5,773,666 discloses a hydroformylation process using $P(X_1)(X_2)(X_3-SO_3M)$ as a ligand, wherein $X_1$ and $X_2$ are monovalent hydrocarbon groups with 1-15 carbon atoms, $X_3$ is a divalent hydrocarbon group with 1-15 carbon atoms, and M is an alkali metal. In the description and working examples of U.S. Pat. No. 5,773,666, $X_3$ is disclosed to be specifically 1,3-phenylene or a tri- or tetra-methylene, such that the phenylene or the tri- or tetra-methylene is substituted with a sulfonate group.

U.S. Pat. No. 5,180,854 discloses sulfonated organophosphine ligands of the following generic formula:

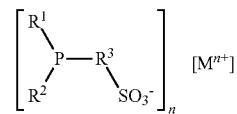

wherein $R^3$ represents a divalent alkylene radical having from 2 to 12 carbon atoms or a divalent 1,3-phenylene radical.

Preferably, when $R^3$ is a divalent alkylene radical, $R^3$ has from 2 to 5 carbon atoms; more preferably, $R^3$ is, 1,3-propylene or 1,4-butylene.

T. Bartik, et al. discloses in *Organometallics*, 12 (1993), 164-170, water-soluble phosphines prepared by sulfonating one or more phenyl groups on a tri(aralkyl)phosphine of the formula $P[(CH_2)_x(C_6H_5)]_3$, wherein x is 1, 2, 3, or 6.

U.S. Pat. No. 4,625,068 and U.S. Pat. No. 4,642,388 disclose the use of non-ionic tricycloalkylphosphines, such as tricyclohexylphosphine, in hydroformylation of internal olefins or hindered terminal vinylidenes, respectively.

SUMMARY OF THE INVENTION

In one aspect, this invention provides for a novel class of sulfonated triorganophosphine compounds represented by Formula I:

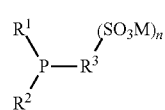

(I)

wherein $R^1$ and $R^2$ each individually represent a monovalent hydrocarbyl or substituted hydrocarbyl radical selected from alkyl, aralkyl, and alicyclic radicals; wherein $R^3$ represents a divalent or polyvalent alkylene or a divalent or polyvalent alicyclic radical (hereinafter, "alkylene radical"), which is bonded to the phosphorus atom and to one or more sulfonate substituents; wherein $R^3$ does not contain any aryl moieties; and wherein M comprises a monovalent cation, n is an integer representing a total number of sulfonate substituents, advantageously, from 1 to 3. As a further requirement, each of $R^1$, $R^2$, and $R^3$ are "bulky" radicals, which means that in each of $R^1$, $R^2$, and $R^3$ the carbon atom attached to the phosphorus atom or a carbon atom directly bonded to the carbon atom attached to the phosphorus atom is additionally bonded to at least 2 other carbon atoms. The aforementioned requirement ensures that $R^1$, $R^2$, and $R^3$ have branching carbon chains that provide for steric bulk.

In a second aspect, this invention provides for a novel complex catalyst or complex catalyst precursor composition comprising a Group 8-10 (formerly Group VIII) transition metal bonded to at least one molecule of ligand comprising Formula I hereinabove, the transition metal optionally being further bonded to carbon monoxide, hydrogen, or both carbon monoxide and hydrogen.

In a third aspect, this invention provides for a novel complex catalyst solution or complex catalyst precursor solution comprising a solvent, a complex catalyst or catalyst precursor composition comprising a Group 8-10 transition metal bonded to at least one molecule of ligand, and optionally further comprising free ligand, wherein the bonded and free ligands are represented by Formula I hereinabove; and wherein optionally the Group 8-10 transition metal can be further bonded to carbon monoxide, hydrogen, or both carbon monoxide and hydrogen.

The following advantages of the invention are mentioned; but should not in any manner place limits on the invention. At the start, the ionically-charged class of compounds claimed herein possesses sufficient water solubility or solubility in appropriate mixtures of water and non-aqueous polar solvents, such that said ionically-charged compound(s) can be easily separated from one or more non-polar reaction products. The separation involves addition of water to the product fluid with subsequent formation of two immiscible liquid phases, one of which is the product phase and the other of which is the catalyst-containing phase. This advantage renders the claimed class of compounds useful for certain hydroformylation processes detailed hereinafter. Accordingly, the novel catalyst composition and novel solution claimed herein comprising the ionically-charged ligand composition of this invention find utility, particularly, in the hydroformylation of long-chain olefinically-unsaturated compounds having from 6 to about 60 carbon atoms, preferably, from about 10 to about 50 carbon atoms, such as, olefinically-unsaturated fatty acids or fatty esters derived from seed oils. Beneficially, the novel hydroformylation catalyst of this invention provides for comparable olefin conversion and product selectivity as compared with prior art catalysts containing ionically-charged ligands. Moreover, the novel composition provides for improved ligand stability and improved ligand and rhodium recovery and recycling, as compared with prior art ligands containing one or more aryl-phosphorus bonds. Indeed, one of the essential decomposition mechanisms of the prior art ligands involves alkyl-aryl exchange by reaction of an olefin with the aryl radical directly attached to the phosphorus atom. The class of compounds claimed in this invention does not comprise an aryl-phosphorus bond, but rather contains phosphorus bonded only to bulky alkyl groups, thereby essentially eliminating the possibility of alkyl-aryl exchange. Additionally, the bulky alkyl groups $R^1$, $R^2$, and $R^3$ provide for acceptable ligand concentration effect on process reaction rate, which means that a change in ligand concentration does not unacceptably alter the reaction rate.

In a fourth aspect, this invention provides for a novel hydroformylation process comprising contacting one or more olefinically-unsaturated compounds with carbon monoxide and hydrogen in the presence of a Group 8-10 transition metal-ligand complex catalyst, wherein the ligand is represented by the composition of Formula I hereinabove, the contacting being conducted under process conditions sufficient to prepare one or more corresponding aldehyde products. The novel hydroformylation process of this invention finds utility in the production of useful organic intermediates, solvents, and monomers, particularly, mono-, di-, and tri-alcohols and amines. These monomers can be converted via transesterification into polyester polyols and polyester polyamines that find utility in the manufacture of polyurethane polymers.

BRIEF DESCRIPTION OF THE DRAWINGS

As shown in FIG. 1, the intermediate is used in preparing sodium 3-(dicyclohexylphosphino)cyclohexane-1-sulfonate.

DETAILED DESCRIPTION OF THE INVENTION

Figure 1:
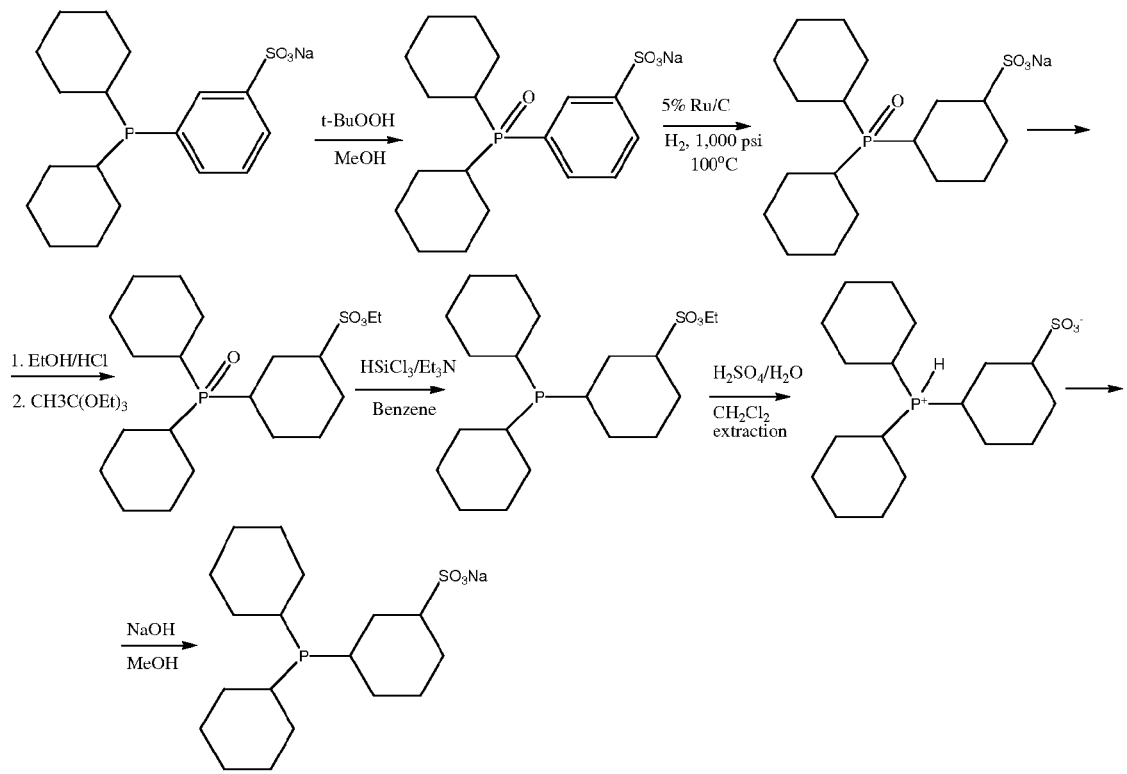
FIG. 1 illustrates a synthetic scheme for preparing sodium 3-(dicyclohexylphosphino)cyclohexane-1-sulfonic acid from sodium 3-(dicyclohexyl-phosphino)benzenesulfonate.

Certain phrases, terms, and words used in this Application are defined hereinafter. When interpreting a meaning of a phrase, term, or word, its definition here governs, unless for a particular use, a different meaning is stated elsewhere in this specification or unless a context of the use of the phrase, term, or word clearly indicates a different meaning is intended from the definitions provided herein.

The articles "a" and "the" refer to singular and plural forms of what is being modified by the articles. When used in front of a first member of a list of two or more members, the words "a" and "the" independently refer to each member in the list. As used herein, "a," "an," "the," "at least one," and "one or more" are used interchangeably. The term "comprises" and variations thereof do not have a limiting meaning where these terms appear in the description and claims. Thus, for example, a reactant mixture that comprises an olefin can be interpreted to mean that the olefin includes one or more olefins.

All percentages, preferred amounts or measurements, ranges and endpoints thereof are inclusive, that is, "a range from 5 to 10" includes 5 and 10. "At least" is equivalent to "greater than or equal to," and "at most" is, thus, equivalent to "less than or equal to." Numbers herein have no more precision than stated. Thus, "115" includes at least from 114.6 to 115.4. All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus, a range that has an advantageous lower limit combined with a most preferred upper limit is preferred for the practice of this invention. The term "advantageously" is used to denote a degree of preference more than required, but less than is denoted by the term "preferably."

Unless stated otherwise, when an element, material, or step capable of causing undesirable effects is present in amounts or in a form such that it does not cause the effect to an unacceptable degree, that element, material, or step is considered substantially absent for the practice of this invention. Those skilled in the art recognize that acceptable limits vary with equipment, conditions, applications, and other variables, but are determinable without undue experimentation in each situation where they are applicable. In some instances, variation or deviation in one parameter is acceptable to achieve another desirable end.

As used herein, the phrase "having the formula" or "represented by the formula" is not intended to be limiting and is used in the same manner as the term "comprising" is commonly used.

The term "comprising," is synonymous with "including," "containing," or "characterized by," is inclusive or open-ended and does not exclude additional, unrecited elements, material, or steps. The term "consisting essentially of" indicates that in addition to specified elements, materials, or steps, unrecited elements, materials or steps are optionally present in amounts that do not unacceptably materially affect at least one basic and novel characteristic of the subject matter. The term "consisting of" indicates that only stated elements, materials or steps are present except that unrecited elements, materials or steps are optionally present to an extent that has no appreciable effect, or are substantially absent.

The word "optionally" means "with or without," that is, not mandatory and left to one's choice. As an example, to say "optionally, a non-polar solvent" means with or without a non-polar solvent.

The number of carbon atoms or a range thereof forming a moiety or compound is defined by prefixing the moiety or compound with a formula "$C_m$" or "$C_m$-$C_n$," respectively, wherein m and n are integers. For example, a $C_1$-$C_{10}$ hydrocarbyl means the hydrocarbyl has a number of carbon atoms in a range from one (1) to ten (10) carbon atoms.

Abbreviations and symbols "g," "h," "L," "ml," "mol," "mmol," "NMR," "° C.," "psia (kPa)," and "%" are used, respectively, for "gram," "hour" "liter," "milliliter," "mole," "millimole," "nuclear magnetic resonance," "degree Celsius," "pounds per square inch absolute (kilopascals), and "percent," respectively, and plural forms thereof.

For the purposes of this invention, all citations herein to chemical Group(s) and elements are referenced with respect to *IUPAC Nomenclature of Inorganic Chemistry: IUPAC Recommendations* 2005, Royal Society of Chemistry, 2005, edited by N. G. Connelly and T. Damhus. (For correspondence with the former recommendation, see Periodic Table of the Elements, *CRC Handbook of Chemistry and Physics, 75th* ed., Press, 1994.)

The relevant teachings of each reference cited herein are incorporated to the maximum extent allowed by United States law. In the event of a conflict between a portion of an incorporated reference and this Application, this Application takes precedence.

In the detailed description that follows, several chemical terms are frequently used, which for clarity are defined herein.

The term "hydrocarbyl" refers to univalent organic radicals comprised of carbon and hydrogen atoms and containing from about 1 to about 30 carbon atoms, preferably, from 1 to about 12 carbon atoms, including linear, branched, cyclic, saturated and unsaturated species, such as alkyl, alicyclic, alkenyl, aryl, alkaryl, and aralkyl groups. The term "substituted hydrocarbyl" refers to a hydrocarbyl radical that is substituted with one or more substituents disclosed hereinafter.

The term "hydrocarbylene" refers to a divalent hydrocarbyl radical. The term "alkyl" refers to a saturated monovalent hydrocarbyl radical, which can be linear, branched, or cyclic (alicyclic). If linear or branched, the radical advantageously contains from 1 to about 30 carbon atoms, for example, methyl, ethyl, propyl, isopropyl, butyl, iso-butyl, tert-butyl, and the like. If cyclic (alicyclic), the radical advantageously contains from 4 to about 8 carbon atoms, such as cyclobutyl, cyclopentyl, cyclohexyl, cycloheptyl, and cyclooctyl. Preferably, the linear or branched alkyl radical contains from about 1 to about 12 carbon atoms; and the alicyclic radical contains from about 5 to about 7 carbon atoms, exclusive of carbon-containing substituents.

The term "alkylene" as used herein refers to a linear, branched, or cyclic divalent alkyl radical.

As used herein the term "aromatic" refers to a polyatomic, cyclic, conjugated ring system containing $(4\delta+2)\pi$-electrons, wherein $\delta$ is an integer greater than or equal to 1. The term "fused" as used herein with respect to a ring system containing two or more polyatomic, cyclic rings means that with respect to at least two rings thereof, at least one pair of adjacent atoms is included in both rings. The term "aryl" refers to a monovalent aromatic substituent which may be a single aromatic ring or multiple aromatic rings that are fused together, linked covalently, or linked to a common group such as a methylene or ethylene moiety. Examples of aromatic ring(s) include phenyl, naphthyl, anthracenyl, and biphenyl, among others. Preferred aryl radicals contain one aromatic ring.

The term "arylene" refers to a divalent aryl radical.

The term "aralkyl" or "arylalkyl" refers to a monovalent alkyl radical substituted with at least one aryl radical. The term "aralkylene" refers to a divalent alkylene radical substituted with at least one aryl radical.

The term "arylalicyclic" refers to an alicyclic radical substituted with at least one aryl group. An example of an arylalicyclic radical is "phenylcyclohexyl" or "phenylcyclopentyl." Advantageously, the arylalicyclic radical contains greater than about 10 carbon atoms and less than about 20 carbon atoms.

The term "alkaryl" refers to a monovalent aryl radical with one or more alkyl substituents. The term "alkarylene" refers to a divalent aryl radical with one or more alkyl substituents.

As used herein, any and all of the terms "hydrocarbyl," "hydrocarbylene," "alkyl," "aromatic," "alkylene," "aryl," "arylene," "alkaryl," "alkarylene," "aralkyl," "aralkylene," "alicyclic," and "arylalicyclic" are intended to include substituted variants thereof. The term "substituted" or the words "substituted variants thereof" refer to the replacement of at least one hydrogen atom that is bonded to a carbon atom, for example, an alkyl or aryl carbon atom, with a non-hydrogen moiety, preferably, a heteroatom or heteroatom-containing substituent, more preferably selected from halogens (preferably F) nitrogen, oxygen, and phosphorus.

The presence of one or more substituents on any particular radical will increase the valency of that radical by one or more. For example, if a divalent alkylene radical, e.g., $R^3$, is substituted with one or more substituents, the valency of the alkylene radical will increase to trivalent or polyvalent, respectively. Other substituents that can be present, besides the sulfonate, on any of the radicals include, without limitation, halogen (more preferably, F), phosphonyl, $C_{1-20}$ alkylamido, imino, hydroxyl, $C_{1-20}$ alkoxy, $C_{5-20}$ aryloxy, $C_{2-20}$ alkoxycarbonyl, $C_{5-20}$ aryloxycarbonyl, formyl, acyl, cyano, cyanato, carbamoyl, epoxy, silyl, silyloxy, silanyl, siloxazanyl, and the hydrocarbyl moieties $C_{1-20}$ alkyl, $C_{2-20}$ alkenyl, $C_{2-20}$ alkynyl, $C_{5-20}$ aryl, $C_{5-30}$ aralkyl, and $C_{5-30}$ alkaryl; preferably, cyano, fluoro, trifluoromethyl, trialkylsilyl, alkoxy, carboalkoxy (ester), dialkyl amino, dialkylamido, more preferably, where appropriate in the aforementioned preferred list having $C_{1-15}$ carbon atoms. In addition, the aforementioned functional groups can, if a particular group permits, be further substituted with one or more additional functional groups or with one or more hydrocarbyl moieties, such as those specifically enumerated above.

In one aspect, this invention provides for a novel class of sulfonated triorganophosphine compounds represented by Formula I:

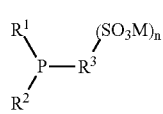

(I)

wherein $R^1$ and $R^2$ each individually represent a monovalent hydrocarbyl or substituted hydrocarbyl radical selected from alkyl, aralkyl, and alicyclic radicals; wherein $R^3$ represents a divalent or polyvalent alkylene or a divalent or polyvalent alicyclic radical (hereinafter, "alkylene radical"), which is bonded to the phosphorus atom and to one or more sulfonate substituents; wherein $R^3$ does not contain any aryl moieties; and wherein M comprises a monovalent cation, n is an integer representing a total number of sulfonate substituents, advantageously, from 1 to 3. As a further requirement, each of $R^1$, $R^2$, and $R^3$ are "bulky" radicals, which means that in each of $R^1$, $R^2$, and $R^3$ the carbon atom attached to the phosphorus atom or a carbon atom directly bonded to the carbon atom attached to the phosphorus atom is additionally bonded to at least 2 other carbon atoms. The aforementioned requirement ensures that $R^1$, $R^2$, and $R^3$ have branching carbon chains that provide for steric bulk. While not intending to bind the invention to any theory, it is believed that the bulky radicals may provide for hydroformylation catalysts comprising only one organophosphine ligand per transition metal atom (as opposed to a plurality of ligands per transition metal atom), which in turn may lead to improved catalyst activity.

In a preferred embodiment, $R^1$ and $R^2$ are each individually a monovalent hydrocarbyl or substituted hydrocarbyl radical containing from 3 to about 30 carbon atoms selected from alkyl, aralkyl, and alicyclic monovalent radicals, with branching at the carbon attached to the phosphorus atom or branching at the carbon adjacent to the carbon attached to the phosphorus atom so as to provide for steric bulk. Preferably, the alkyl radicals contain from 3 to about 12 carbon atoms, while the aralkyl radical contains from about 6 to about 12 carbon atoms. The alicyclic radical can be mono-cyclic, bi-cyclic, or poly-cyclic and preferably, contains from about 3 to about 10 carbon atoms, exclusive of carbon-containing substituents on the ring(s). An illustrative, but non-limiting, list of alkyl radicals represented by the $R^1$ and $R^2$ includes iso-propyl, iso-butyl, sec-butyl, tert-butyl, 2,2-dimethylpropyl, 2-methylbutyl, 1,1-dimethylpropyl, 2-ethylhexyl. Arylalkyl radicals include, without limitation, benzyl, 2-methylbenzyl, 2,6-dimethylbenzyl, 1-phenylethyl, phenylcyclohexyl, 1,2,3,4-tetrahydronaphthyl, phenylcyclopentyl; alicyclic radicals include, without limitation, cyclopentyl, cyclohexyl, cycloheptyl, cyclooctyl, ethylcyclohexyl, norbornyl, adamantyl, and dicyclopentyl. Moreover, such monovalent hydrocarbon radicals can be substituted with any substituent that does not adversely change the desired result(s) of this invention. Illustrative substituents that can be bound to the monovalent hydrocarbyl radical include those substituents mentioned hereinabove, preferably, cyano, fluoro, trifluoromethyl, trialkylsilyl, alkoxy, carboalkoxy (ester), dialkyl amino, and dialkylamido, preferably, having 1 to about 15 carbon atoms where appropriate. Even more preferably, $R^1$ and $R^2$ are each individually selected from branched chain alkyl radicals having from 3 to about 10 carbon atoms or alicyclic radicals having from 6 to about 10 carbon atoms, including iso-propyl, iso-butyl, neo-pentyl, cyclohexyl, norbornyl, and adamantyl. Most preferably, $R^1$ and $R^2$ each individually represent a cyclohexyl or iso-propyl radical, especially, cyclohexyl.

Preferably, $R^3$ in Formula I is selected from divalent and polyvalent, alicyclic radicals having from 6 to about 10 carbon atoms and alkylene radicals having greater than 3 and less than about 10 carbon atoms, which optionally can be substituted with substituents such as those mentioned above, preferably, halide (F), alkoxy, cyano, and/or alkyl groups. $R^3$ is further required to have at least one sulfonate (—$SO_3^-$) ion attached directly to the $R^3$ group. A non-limiting list of $R^3$ diradicals (polyradicals) suitable for this invention is set forth hereinafter:

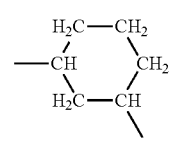

II

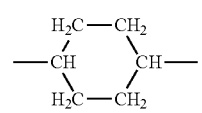

III

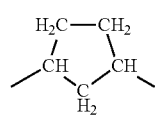

IV

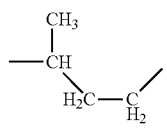

V

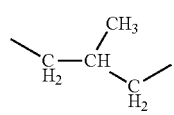

VI

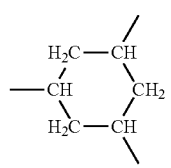

VII

Preferably, n in Formula I is 1 or 2. Preferably, M in Formula I represents a metal cation selected from the group consisting of alkali metal ions. Illustrative alkali metal ions include lithium ($Li^+$), sodium ($Na^+$), potassium ($K^+$), rubidium ($Rb^+$), and cesium ($Cs^+$). More preferably, M is sodium or potassium ion.

Preferred sulfonated tertiary phosphine metal salt compounds of Formula I include the following. In these preferred structures, any other monovalent metal cation, more preferably, another alkali metal ion, may replace the alkali ion illustrated.

Ligand 1

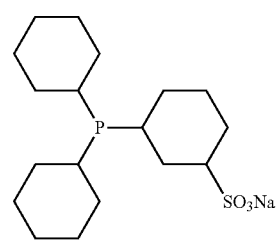

Ligand 2

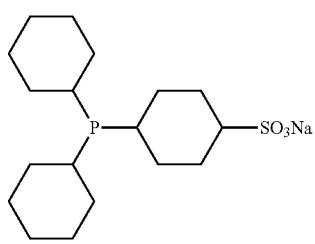

Ligand 3

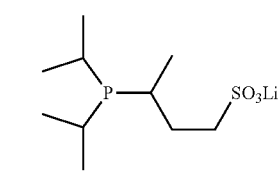

Ligand 4

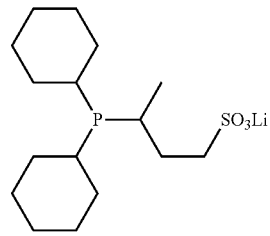

Ligand 5

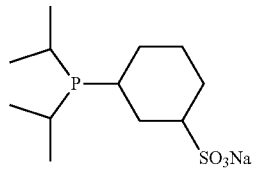

Ligand 6

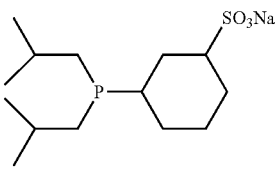

Ligand 7

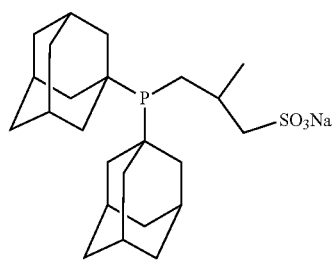

Ligand 8

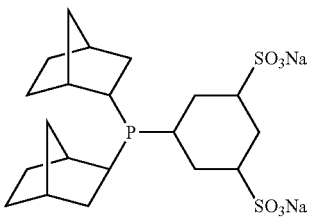

Ligand 1 is most preferred, because it structurally mimics sodium 3-(dicyclohexylphosphino)benzene sulfonate which is a preferred prior art ligand for hydroformylation catalysts; however, Ligand 1 contains a cyclohexyl ring in place of the phenyl ring of the prior art ligand thereby eliminating the possibility of alkyl-aryl exchange. Thus, the ligand of this invention retains most of the physical and chemical properties of the prior art ligand essential for catalyst separation and recycling, namely, solubility, partitioning between different phases, and acceptable surfactant properties, but without the detrimental alkyl-aryl exchange feature.

The synthesis of the ionically-charged triorganophosphine compound of this invention depends upon whether $R^3$ is chosen to be an alicyclic group or a branched alkylene group. The synthesis is first described for the case wherein $R^3$ is a divalent alicyclic group, such as cyclohexylene. In this synthesis, a first step comprises preparation of a precursor organophosphine compound $R^4R^5PR^6$—$(SO_3M)_n$, wherein $R^4$ is either $R^1$ or its aromatic analog, $R^5$ is either $R^2$ or its aromatic analog, and $R^6$ is a divalent or polyvalent arylene radical corresponding to its divalent or polyvalent saturated analog $R^3$, wherein $R^1$, $R^2$, and $R^3$ are defined hereinbefore; and wherein M and n have the definitions given hereinabove. As an example, if the desired $R^1$ and $R^2$ are each independently cyclohexyl and $R^3$ is desirably cyclohexylene, then $R^4$ and $R^5$ are each independently cyclohexyl (1$^{st}$ case) or phenyl (2$^{nd}$ case) and $R^6$ is phenylene. The preparation of the precursor organophosphine in the first case is known in the art, as described for example, in International Patent Application Publication WO 2007035540 incorporated herein by reference. The precursor organophosphine in the second case, preferably, 3-(diphenylphosphino)benzenesulfonate, is available from commercial sources.

Advantageously, it is desired to convert $R^6$ to its saturated analog $R^3$ in the first case and $R^4$, $R^5$, and $R^6$ to their saturated analogs $R^1$, $R^2$, and $R^3$, respectively, in the second case, via hydrogenation. The direct hydrogenation of the aryl group under hydrogen in the presence of a hydrogenation catalyst, such as a platinum metal, is not readily accomplished, however, because the precursor organophosphine $R^4R^5PR^6$—$(SO_3M)_n$ tends to poison the hydrogenation catalyst. Since phosphine oxides tend not to poison hydrogenation catalysts, the second step of the synthesis converts the organophosphine precursor $R^4R^5PR^6$—$(SO_3M)_n$ to its corresponding phosphine oxide (phosphinyl). Thus, the organophosphine precursor is contacted with an organic hydroperoxide, such as t-butyl hydroperoxide, ethylbenzene hydroperoxide, or cumene hydroperoxide, at a temperature ranging from about 0° C. to about 50° C. and advantageously about atmospheric pressure to obtain the corresponding phosphine oxide $R^4R^5P(O)R^6(SO_3M)_n$, wherein $R^4$, $R^5$, $R^6$, M, and n have the same definitions as given hereinbefore. Progress of the reaction can be readily followed by $^{31}P$ nuclear magnetic resonance spectroscopy ($^{31}P$ NMR), wherein a resonance attributed to a trivalent phosphorus atom of the phosphine precursor decreases, while a resonance attributed to a pentavalent phosphorus atom of the phosphine oxide increases. The art describes such phosphine oxidations, for example, in Y. Yamamoto, S.-U. Rehman, *Chemical Letters*, 1984, 1603-1606, incorporated herein by reference.

In a second step, the aryl ring $R^6$ in case 1 and aryl rings $R^4$, $R^5$, and $R^6$ in case 2 are now hydrogenated to form a phosphinyl compound having the corresponding saturated radicals $R^1$, $R^2$, and $R^3$, respectively; that is to yield a compound of formula $R^1R^2P(O)R^3(SO_3M)_n$, wherein $R^1$, $R^2$, $R^3$, M, and n have the definitions given hereinbefore. The hydrogenation is advantageously conducted under hydrogen gas in the presence of a hydrogenation catalyst, such as a Group 8, 9, and/or 10 metal supported on a suitable support. Group 8-10 metals include iron, cobalt, nickel, ruthenium, rhodium, palladium, osmium, iridium, and platinum. Suitable supports include carbon, silica, alumina, and aluminosilicates. A preferred catalyst comprises ruthenium supported on carbon. Preferably, the Group 8-10 metal is loaded onto the support in a quantity ranging from about 1 to about 10, more preferably about 5, weight percent. The hydrogenation is advantageously conducted at a temperature ranging from about 50° C. to about 200° C., preferably, from about 80° C. to about 150° C., under a hydrogen at a pressure ranging from about 200 psia (1,379 kPa) to about 2000 psia (13,790 kPa), preferably, from about 700 psia (4,826 kPa) to about 1,500 psia (10,342 kPa). The reaction can be followed by $^1H$ NMR by observing the disappearance of the aromatic protons attributed to $R^6$ and, optionally, $R^4$ and $R^5$ depending upon whether these are also aryl groups, and the appearance of saturated ring protons attributed to $R^3$, and optionally, $R^1$ and $R^2$. $^{31}P$ resonances for cis and trans isomers of the hydrogenated products can also be observed. The art describes such hydrogenation reactions as found, for example, in Y. Yamamoto, S.-U. Rehman, *Chemical Letters*, 1984, 1603-1606, incorporated herein by reference.

In the third step, the alkali metal salt of the phosphinyl sulfonate $R^1R^2P(O)R^3(SO_3M)_n$ is converted to the corresponding alkyl sulfonate ester of formula $R^1R^2P(O)R^3(SO_3R^7)_n$, wherein each $R^7$ comprises a monovalent $C_{1-5}$ alkyl radical. A conventional protocol for converting sulfonic acids to sulfonate alkyl esters is readily adapted to the present case. Such protocols have been described by C. Larpent, et al., *Synthesis Communications*, 1991, 21, 495-503, and J. I. Trujillo and A. S. Gopalan, *Tetrahydron Letters*, 1993, 32, 7355-7358, both references incorporated herein by reference. Advantageously, the procedure involves contacting the sulfonated salt $R^1R^2P(O)R^3(SO_3M)_n$ with "n" equivalents of trialkylorthoacetate or equivalent alkyl-transfer reagent. A preferred trialkylorthoacetate is a tri-($C_{1-3}$ alkyl)orthoacetate, more preferably, triethylorthoacetate. The sulfonated salt is advantageously dissolved in an appropriate solvent, such as an alcohol, acidified with a conventional acid, such as hydrochloric acid; after which the trialkylorthoacetate dissolved in a suitable organic solvent, such as a chlorinated hydrocarbon, for example, dichloromethane, is added to the solution containing the sulfonated salt. Refluxing the resulting solution at a temperature from about 15° C. to about 100° C. under about atmospheric pressure for a time from about 3 hours to about 20 hours is advantageously sufficient to effect complete esterification. The product is worked up via conventional techniques that first involve neutralization of the acid, then extraction of the reaction solution with water to obtain the esterified product $R^1R^2P(O)R^3(SO_3R^7)_n$ from the organic phase. Later, the ester group(s), which is (are) inert with respect to the subsequent synthesis steps, is (are) readily cleaved under non-oxidizing conditions according an acceptable solubility of the product in organic solvents.

In a fourth step, the esterified product $R^1R^2P(O)R^3(SO_3R^7)_n$ is subjected to reduction to convert the phosphine oxide (phosphinyl) back to the corresponding phosphine $R^1R^2PR^3(SO_3R^7)_n$. The art describes similar reductions, as found for example in K. Yamamoto and S.-U. Rehman, *Chemical Letters*, 1984, 1603-1606, and H. Yamamoto, et al., *Chemical Letters*, 1989, 349-352, both incorporated herein by reference. The reduction involves reaction of the phosphine oxide sulfonic ester, dissolved in an appropriate hydrocarbon solvent, such as benzene, with an excess of a reducing agent, such as, sodium borohydride or a trihalosilane. Trichlorosilane is preferred. The silane is used advantageously in a 2 to about 15 mole excess with respect to the phosphine oxide sulfonic ester. The reaction is advantageously conducted under an oxygen-free atmosphere, such as a blanket of nitrogen or helium or argon, to protect the oxygen-sensitive phosphine product. Cooling may be required, or slight heating to a temperature no higher than about reflux at about atmospheric pressure can be used; and the reaction is advantageously quenched with water. The phosphine product is recovered by conventional techniques, for example, extraction and drying.

In a fifth step, the phosphine sulfonic ester $R^1R^2PR^3(SO_3R^7)_n$ is converted via treatment with a conventional acid, such as sulfuric or hydrochloric acid, to cleave the ester group yielding the corresponding sulfonic acid $R^1R^2PR^3(SO_3H)_n$, which can be extracted into a suitable hydrocarbon or chlorinated hydrocarbon solvent, such as methylene chloride. The sulfonic acid can exist as a zwitterion. (The term "zwitterion" (from the German "Zwitter" "hybrid," "hermaphrodite") refers to a chemical compound that is electrically neutral but carries formal positive and negative charges on different atoms. In this instance, the phosphorus atom is protonated and carries a +1 charge, while the sulfonate ion is deprotonated and carries a −1 charge.

Finally, in a sixth step, the phosphine sulfonic acid is converted into its corresponding alkali metal salt via titration of the acid with the appropriate alkali metal hydroxide, preferably, sodium hydroxide, dissolved in a suitable alcoholic solvent, such as a $C_{1-3}$ alcohol, preferably, methanol or ethanol. The alcoholic solvent is then concentrated or removed to yield a solid precipitate identified as the composition of this invention: $R^1R^2PR^3(SO_3M)_n$.

As an illustration of the above broad synthesis, reference is drawn to the figures and examples hereinafter which describe the specific synthesis of sodium 3-dicyclohexylphosphino cyclohexylsulfonate in one manner (case 1) starting from sodium 3-(dicyclohexylphosphino)benzene sulfonate, as illustrated in Example 1 and FIG. 1, and in a second manner (case 2) starting from sodium 3-(diphenylphosphino)phenyl sulfonate, as illustrated in Example 2 and FIG. 2.

Figure 3:
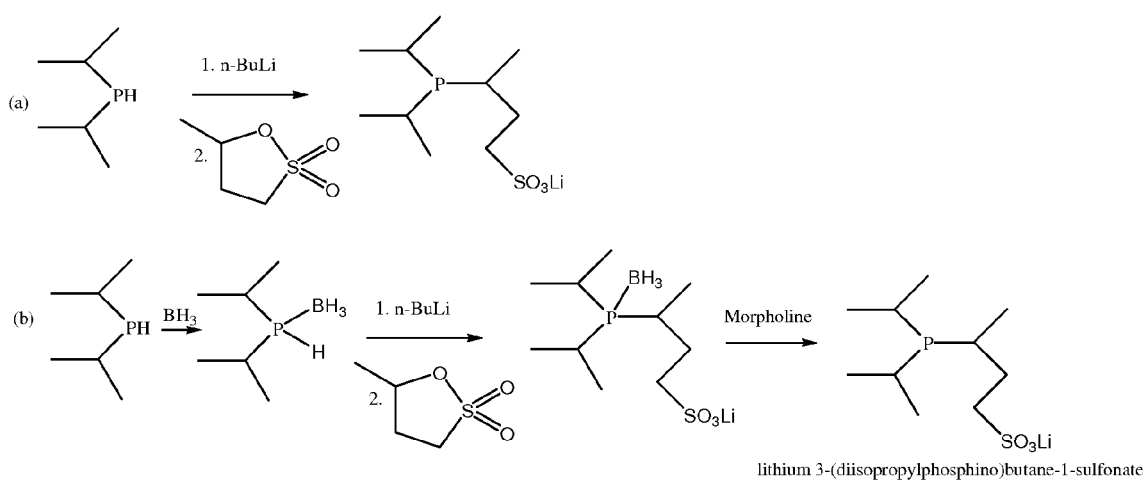
FIG. 3 illustrates a synthetic scheme for preparing lithium 3-(diisopropylphosphino)butane-1-sulfonate.

Synthesis of open-chain analogs comprising (dihydrocarbylphosphino)-(alkane)sulfonates involves a different synthetic methodology. Reference is made to FIG. 3, for a description of the synthesis of lithium 3-(diisopropylphosphino)butane-1-sulfonate (Ligand 3). One synthetic method involves metalation of a dihydrocarbylphosphine, such as diisopropylphosphine, with an alkyl lithium compound, such as n-butyl lithium, followed by reaction with an appropriate sultone, such as 3-methyl-1,3-propane sultone, illustrated in FIG. 3(*a*). Methods for preparing the appropriate sultone are known in the art. For example, 3-methyl-1,3-propane sultone can be prepared by heating crotyl sulfonic acid under vacuum according to U.S. Pat. No. 2,900,393, incorporated herein by reference. This methodology can be further enhanced by using borane-protected intermediates, as illustrated in FIG. 3(*b*), as described for example by J. McNulty and Y. Zhou in *Tetrahedron Letters*, 2004, 45, 407-409, incorporated herein by reference. In contrast to unprotected phosphines, borane-protected phosphines are resistant to oxidation, and the borane-protected sequence makes the preparation overall more efficient. Metalation of the borane-protected dihydrocarbylphosphine with the lithium reagent results in a borane-protected dihydrocarbylphosphide. A coupling reaction of the borane-protected dihydrocarbylphosphide with the corresponding alkane sultone leads to a borane-protected (dihydrocarbylphosphino)(alkane)sulfonate which produces the desired (dihydrocarbylphosphino)(alkane)sulfonate, such as lithium 3-(diisopropylphosphino)butane-1-sulfonate, after deprotection using morpholine.

The intermediates in the above synthetic schemes and the product of this invention can be identified by standard analytical techniques known to the skilled person, for example, $^{31}P$ and/or $^1H$ and/or $^{13}C$ NMR, mass spectrometry (MS), and/or infrared spectroscopy. The purity of the product and any intermediates of the synthesis can be verified by gas chromatography (GC), thin layer chromatography (TLC), high performance liquid chromatography (HPLC), any suitable NMR spectroscopy, including $^1H$, $^{13}C$, and $^{31}P$ NMR, and ionic chromatography (IC).

The composition of this invention of Formula I finds application as a ligand in transition metal-ligand complex catalysts and catalyst precursors that are used in carbonylation processes, preferably, hydroformylation processes. Accordingly, in a second aspect this invention provides for an entirely new class of complex catalysts and complex catalyst precursor compositions that comprise a Group 8, 9, or 10 transition metal bonded to at least one ligand represented by Formula I. Optionally, the Group 8-10 transition metal can also be bonded to carbon monoxide, hydrogen, or both carbon monoxide and hydrogen. The Group 8-10 transition metal that makes up the complex catalyst or catalyst precursor composition of this invention includes transition metals selected from the group consisting of rhodium (Rh), cobalt (Co), iridium (Ir), ruthenium (Ru), iron (Fe), nickel (Ni), palladium (Pd), platinum (Pt), and osmium (Os), and mixtures thereof, with the preferred metals being ruthenium, rhodium, cobalt, and iridium, more preferably, rhodium and cobalt, and most preferably, rhodium. The term "complex" as used herein shall be taken to mean a coordination compound formed by the union of one or more ligands, herein one or more ligands of Formula I, with a Group 8-10 metal. Inherently, the ligand(s) is/are electronically rich, since each ligand possesses one phosphorus donor atom having one available or unshared pair of electrons that is capable of forming a coordinate covalent bond with the Group 8-10 transition metal. The oxidation state of the Group 8-10 metal can be any available oxidation state, both electronically neutral (zero) or electronically deficient (positive valence) that allows for bonding to the ligand. Moreover, the oxidation state of the Group 8-10 transition metal as well as the overall oxidation state of the coordination complex or complex precursor can vary during use in the hydroformylation process. The number of available coordination sites on the Group 8-10 transition metal is well known in the art and can range advantageously from about 4 to about 6. Optionally, the Group 8-10 transition metal can be additionally bonded to carbon monoxide, hydrogen, or both carbon monoxide and hydrogen.

In a third aspect, this invention can be described as a novel transition metal complex catalyst or catalyst precursor solution comprising an organic solvent, a solubilized Group 8-10 transition metal-ligand complex, and optionally, free ligand, wherein the free and bound ligands are represented by Formula I hereinabove. Such novel solutions can be prepared by forming a solution comprising an organic solvent, free ligand, and a Group 8-10 transition metal source material, such as the corresponding transition metal oxide, hydride, carbonyl, salt, or organotransition metal complex described hereinafter; and thereafter subjecting such solution to reaction conditions sufficient to bind at least a portion of the ligand to the Group 8-10 transition metal. Optionally, carbon monoxide and hydrogen can be dissolved in the solution and bonded to the Group 8-10 transition metal.

The Group 8-10 transition metal-ligand complex catalyst of this invention can be synthesized by methods known in the art. For instance, a Group 8-10 transition metal hydridocarbonyl(ligand) catalyst can be preformed and introduced into the reaction medium of a hydroformylation process. Standard identification methods can be used to identify the complex catalyst or catalyst precursor composition, including for example, elemental analysis, mass spectroscopy, infrared spectroscopy, and $^1H$, $^{31}P$, and/or $^{13}C$ NMR spectroscopy, and the like.

Preferably, the Group 8-10 transition metal-ligand complex catalyst of this invention is derived from a Group 8-10 transition metal source material that is introduced into the carbonylation reaction medium for in situ formation of the active catalyst. For example, rhodium source materials, such as, rhodium acetylacetonate, rhodium dicarbonyl acetylacetonate, $Rh_2O_3$, $Rh_4(CO)_{12}$, $[RhCl(CO)_2]_2$, $Rh_6(CO)_{16}$, $Rh(NO_3)_3$, and the like can be introduced into the carbonylation reaction medium along with the ligand for the in situ formation of the active catalyst. In a preferred embodiment, rhodium dicarbonyl acetylacetonate is employed as a rhodium source material and reacted with the ligand in the presence of a solvent to form a rhodium-ligand complex catalyst precursor composition, which is introduced into the reactor along with excess free ligand for the in situ formation of the active catalyst. In any event, it is sufficient for the purpose of this invention to understand that carbon monoxide, hydrogen, and ligand are all ligands that are capable of being complexed with the Group 8-10 transition metal, for example, rhodium, and that an active Group 8-10 transition metal-ligand complex catalyst is present in the reaction medium under the conditions of the hydroformylation process. The reaction conditions sufficient for formation of the complex catalyst or catalyst precursor in most cases will be similar to the hydroformylation reaction conditions described hereinbelow.

In a fourth aspect, this invention provides for a carbonylation process, which comprises contacting an organic compound capable of being carbonylated with carbon monoxide under reaction conditions in the presence of the aforementioned Group 8-10 transition metal-ligand complex catalyst wherein the ligand is represented by Formula I. Such processes can include the carbonylation of organic compounds, such as olefins, acetylenes, alcohols, and activated chlorides, with carbon monoxide, and optionally, either hydrogen, alcohol, amine, or water, as well as ring closure reactions of functionally unsaturated compounds, for example, unsaturated amides, with carbon monoxide. Exemplary carbonylation processes include, for example, simple carbonylation (insertion of carbonyl in absence of other reactants), hydroformylation, hydroacylation (intermolecular and intramolecular), hydrocyanation, hydroamidation, hydroesterification, and hydrocarboxylation processes. In a preferred embodiment, the carbonylation process also contains free ligand in addition to the ligand bonded to the Group 8-10 transition metal. Preferably, the carbonylation process involves a hydroformylation process, more preferably, the hydroformylation of an olefinically-unsaturated compound with carbon monoxide in the presence of hydrogen and the transition metal-ligand complex catalyst under reaction conditions to prepare one or more corresponding aldehydes (or formyl-substituted product(s)). Hydroformylation is also known under various other names including the "oxo" process, the "oxo" reaction, "oxonation," the "Roelen reaction." The processing techniques employed in the hydroformylation process of this invention correspond to any of the known processing techniques employed in conventional hydroformylation processes as described hereinafter.

The successful practice of the hydroformylation process of this invention does not depend and is not predicated upon the precise formula of the catalytically active metal complex species, which can be present in a mononuclear, dinuclear, or higher nuclearity form.

Indeed, the precise formula of the catalytically active metal ligand complex can be difficult to determine analytically. Although not intended to be bound to any theory or mechanistic discourse, it appears that the active catalytic species in its generic form comprises the Group 8-10 transition metal in complex combination with one ligand of Formula I, optionally, further in combination with carbon monoxide. The ultimate composition of the active complex can also contain one or more additional ligands, such as hydrogen, or an anion satisfying the coordination sites or nuclear charge of the Group 8-10 transition metal obtained advantageously from the starting transition metal material. Illustrative additional ligands include alkyl, aryl, substituted aryl, $CF_3^-$, $C_2F_5^-$, $CN^-$, $R'_2PO^-$, $R'P(O)(OH)O^-$ (wherein each R' is alkyl or aryl), $CH_3C(O)O^-$, acetylacetonate, $SO_4^{2-}$, $PF_4^-$, $PF_6^-$, $NO_2^-$, $NO_3^-$, $CH_3O^-$, $CH_2=CHCH_2^-$, $C_6H_5CN$, $CH_3CH=$, $NO$, $NH_3$, pyridine, $(C_2H_5)_3N$, mono-olefins, diolefins, triolefins, tetrahydrofuran, and the like. Of course, the active complex species is preferably free of any additional organic ligand or anion that might poison the catalyst and have an unacceptable adverse effect on the catalyst performance, such as possibly halogen atoms and sulfur atoms with a low degree of oxidation, such as mercaptanes, that may poison the catalyst.

Any amount of complex catalyst can be employed in the hydroformylation process, provided that the amount is sufficient to catalyze the desired hydroformylation reaction. Advantageously, the concentration of complex catalyst provides for a concentration of Group 8-10 transition metal of greater than about 10 parts per million (ppm), preferably, greater than about 25 ppm, by weight calculated as free metal. Advantageously, the concentration of complex catalyst provides for a concentration of Group 8-10 transition metal of less than about 1,000 ppm, preferably, less than about 800 ppm, and more preferably, less than about 600 ppm, by weight calculated as free metal.

The olefinic reactants to be used in the hydroformylation process of this invention can be any terminally or internally olefinically-unsaturated aliphatic hydrocarbon, including straight chain, branched chain, and cyclic formulas. Such olefins contain preferably from 2 to about 60 carbon atoms and one or more unsaturated groups (C=C). Long-chain olefinically-unsaturated aliphatic hydrocarbons having from 6 to about 60 carbon atoms are preferred, and more, preferably, from about 10 to about 50 carbon atoms. Moreover, such olefins can contain substituents that essentially do not adversely interfere with the hydroformylation process, including, for example, carbonyl, carbonyloxy, hydroxy, oxycarbonyl, halo (preferably F), alkyoxy, aryl, haloalkyl, and cyano substituents. Non-limiting examples of suitable olefinic unsaturated reactants include, for example, alpha olefins, internal olefins, alkyl alkenoates, alkenyl alkanoates, alkenyl alkyl ethers, alkenols, olefinically-unsaturated fatty acids, and olefinically-unsaturated fatty acid esters; the latter unsaturated fatty acid and ester species being founding naturally-occurring and genetically modified seed oils. A non-limiting list of suitable olefinically-unsaturated compounds includes ethylene, propylene, 1-butene, 1-pentene, 1-hexene, 1-octene, 1-decene, 1-dodecene, 1-octadecene, 2-butene, 2-methyl propene (isobutylene), isoamylene, 2-pentene, 2-hexene, 3-hexene, 2-heptene, cyclohexene, propylene dimers, propylene trimers, propylene tetramers, 2-ethylhexene, styrene, 3-phenyl-1-propene, butadiene, 1,3-cyclohexadiene, 1,4-cyclohexadiene, 1,7-octadiene, 3-cyclohexyl-1-butene, allyl alcohol, hex-1-en-4-ol, oct-1-ene-4-ol, vinyl acetate, allyl acetate, 3-butenyl acetate, vinyl propionate, 1-vinyl-3-cyclohexene, allyl propionate, allyl butyrate, methyl methacrylate, 3-butenyl acetate, vinyl ether, vinyl methyl ether, allyl ethyl ether, n-propyl-7-octenoate, methyl 1-decenoate, 3-butenenitrile, 5-hexenamide, methyl oleate, castor oil, soybean oil, canola oil, and sunflower oil, including high oleic variations of the aforementioned oils. Mixtures of any of the aforementioned olefinic starting materials can be employed, if desired. Preferably, the hydroformylation is useful for the production of aldehydes by the hydroformylation of alpha olefins containing from 2 to about 60 carbon atoms, or internal olefins containing from 6 to about 50 carbon atoms, and more preferably, from about 10 to about 50 carbon atoms as found in unsaturated fatty acids and unsaturated fatty esters derived from seed oils.

The hydroformylation process of this invention is preferably conducted in the presence of an organic solvent for the Group 8-10 transition metal complex catalyst. Any suitable solvent that does not unduly interfere with the hydroformylation process can be used including those types of solvents commonly used in prior art carbonylation processes. By way of illustration, suitable solvents for rhodium-catalyzed hydroformylation processes include those disclosed, for example, in U.S. Pat. No. 3,527,809; U.S. Pat. No. 4,148,830; U.S. Pat. No. 5,180,854, and U.S. Pat. No. 5,929,289; the aforementioned citations being incorporated herein by reference. Non-limiting examples of suitable solvents include saturated hydrocarbons (e.g., pentane, octane, decane), aromatic hydrocarbons (e.g., benzene, toluene, xylene), ethers (e.g., tetrahydrofuran), nitriles (e.g., benzonitrile, acetonitrile, propionitrile), aldehydes (including higher boiling hydroformylation products and aldehyde liquid condensation products), ketones broadly including piperidones, pyrrolidones and pyrrolidinones (e.g., N-methylpyrrolidinone, N-methyl piperidone, 1,5-dimethyl-2-pyrrolidone, 2-hydroxyethyl pyrrolidone, N-cyclohexyl pyrrolidone), amides (e.g., dimethylformamide, dimethylacetamide, N-dimethylpropionamide), sulfoxides (e.g., dimethyl sulfoxide), sulfones (e.g., dimethyl sulfone, sulfolane), as well as ionic liquids and supercritical carbon dioxide. Mixtures of two or more solvents may also be employed. When the ligand employed is an ionic ligand, like the one disclosed in this invention, it is preferred to use a non-aqueous, aprotic, polar solvent selected from any in the list hereinabove, more preferably, N-methylpyrrolidinone (NMP). When the ligand employed is a non-ionic ligand, like a non-ionic analog of the ionic ligand of this invention, it is preferred to use a nonpolar solvent selected from any in the list hereinabove. The amount of solvent is not especially critical and need only be sufficient to provide the reaction medium with the desired amount of Group 8-10 transition metal concentration. Advantageously, the amount of solvent ranges from about 5 percent to about 95 percent by weight, based on the total weight of the reaction medium.

Optionally, the hydroformylation process of this invention can be conducted in the presence of free ligand of Formula I, that is, ligand that is not complexed with the Group 8-10 transition metal. The use of free ligand is preferred. While it can be preferred in some instances to employ a free ligand that is identical to the ligand complexed to the transition metal in the Group 8-10-ligand complex catalyst, it is not absolutely required for the free and complexed ligands to be identical. The free and complexed ligands can be different species falling within the scope of Formula I. While the carbonylation process of this invention can be carried out in any excess amount of free ligand, advantageously at least one mole of free ligand per mole of Group 8-10 transition metal is present in the reaction medium. For most purposes, preferably, the amount of ligand per mole of Group 8-10 transition metal is greater than about 1.1/1, more preferably, greater than about 1.3/1 is employed. Preferably, the amount of ligand per mole of Group 8-10 transition metal is less than about 100/1, more preferably, less than about 50/1. The aforementioned ratios correspond to the sum of both the free and complexed ligand. Make-up ligand can be added during the hydroformylation process at any time and in any suitable manner, so as to maintain a predetermined concentration of free ligand in the reaction medium.

The reaction conditions for effecting hydroformylation can be chosen from any of those conditions conventionally used for such processes. The total gas pressure of hydrogen, carbon monoxide, and olefinic unsaturated reactant in the hydroformylation process can range from greater than about 1 psia (7 kPa) to less than about 10,000 psia (68,948 kPa). Preferably, the total pressure of hydrogen, carbon monoxide, and olefinic unsaturated reactant is less than about 2,000 psia (13,790 kPa), and more preferably, less than about 1,500 psia (10,342 kPa). More specifically, the carbon monoxide partial pressure of the hydroformylation process of this invention is advantageously greater than about 1 psia (7 kPa), preferably, greater than about 3 psia (21 kPa). The carbon monoxide partial pressure of the hydroformylation process of this invention is advantageously less than about 1,000 psia (6,8948 kPa), preferably, less than about 750 psia (5171 kPa). The hydrogen partial pressure is advantageously greater than about 5 psia (35 psia), preferably, greater than about 10 psia (69 kPa). The hydrogen partial pressure is advantageously less than about 1,000 psia (6,8948 kPa), preferably, less than about 750 psia (5171 kPa). Advantageously, the $H_2$/CO molar ratio of gaseous hydrogen to carbon monoxide can be greater than about 1/10, and preferably, equal to or greater than about 1/1. The $H_2$/CO molar ratio can be less than about 100/1, and preferably, equal to or less than about 10/1.

Further to the hydroformylation process of this invention, the reaction temperature will depend upon the particular olefinic reagent and carbonylation (e.g., hydroformylation) catalyst employed, as well as the efficiency desired. Advantageously, hydroformylations at reaction temperatures of greater than about 30° C., and preferably, greater than about 40° C., are suitable. Advantageously, hydroformylations at reaction temperatures of less than about 150° C., and preferably, less than about 130° C. are suitable.

The hydroformylation process of this invention can be carried out in the liquid or gas phase, preferably, in one liquid phase, which can more preferably involve a continuous liquid phase recycle stream comprising the transition metal-ligand complex catalyst and any free ligand back to the hydroformylation reactor.

In the preferred hydroformylation process of this invention, the olefin conversion is advantageously greater than about 70 mole percent, preferably, greater than about 80 mole percent. For the purposes of this invention, "olefin conversion" is defined as the mole percentage of olefin feed converted to all products. Olefin conversion will vary depending upon the specific olefin reactant, the specific form of the catalyst, and the specific process conditions employed.

Likewise, in the preferred hydroformylation process of this invention, the selectivity to aldehyde product(s) is advantageously greater than about 60 mole percent, preferably, greater than about 70 mole percent, and more preferably, greater than about 80 mole percent. For the purposes of this invention, "selectivity" is defined as the mole percentage of aldehyde product produced, based on the moles of olefin converted. Again, the selectivity to aldehyde(s) will vary depending upon the specific olefin reactant, the specific form of the catalyst, and the specific process conditions employed.

In the preferred process wherein the reactant olefin comprises one or more long-chain olefinically-unsaturated compounds, preferably, a mixture of unsaturated fatty acids or fatty acid esters, the effluent stream from the hydroformylation reactor can be treated with water so as to induce phase separation to produce a polar phase comprising water, non-aqueous organic solvent, e.g., N-methylpyrrolidinone, the transition metal-ligand complex catalyst, and optional free ligand, wherein the complexed and free ligands are ionically-charged ligands of Formula I, and a non-polar phase comprising one or more formyl-substituted products, preferably one or more formyl-substituted fatty acids or fatty acid esters, and optionally any non-polar solvent(s) as may be present. The polar phase is advantageously recycled back to the reactor, while the non-polar phase is worked up to recover purified aldehyde product(s) for downstream use. Representative art disclosing this type of separation method is found in U.S. Pat. No. 5,180,854 and WO 2004/096744, incorporated herein by reference.

The following examples are illustrative of the present invention and are not to be regarded as limiting thereof. Variations in operational parameters, such as reactants, process conditions, forms of the transition metal-ligand complex catalyst, and ligand species, all falling within the scope of the claims, will be apparent to those skilled in the art based on the description and examples contained herein. All of the parts, percentages, and proportions are given by mole percent, unless otherwise indicated.

Example 1

Preparation of Ligand 1 (with Reference to FIG. 1)

(1) Preparation of Sodium 3-(Dicyclohexylphosphinyl)benzenesulfonate (DCHPOPS-Na)

Sodium 3-(dicyclohexylphosphino)benzenesulfate (DCHPPS-Na) is prepared according to the synthetic procedure described in WO 2007035540. The thus-prepared DCHPPS-Na (11.4 g; 30 mmoL) is dissolved in methanol (100 mL) and stirred overnight at room temperature with tert-butyl hydroperoxide (3.63 g of 90% solution; 36 mmoL). Reaction completion is established by HPLC. The solvent is removed on a rotary evaporator, and the residue is washed twice with hexane (10 mL) and then dried in vacuum to yield sodium 3-dicyclohexylphosphinyl benzenesulfonate (DCHPOPS-Na). Yield 11.8 g (99%). $^{31}P\{^1H\}$ NMR ($CH_3OD$, ppm): 50.16.

(2) Preparation of Sodium 3-(dicyclohexylphosphinyl)cyclohexane-1-sulfonate

DCHPOPS-Na (3.00 g), prepared as above, is dissolved in dry methanol (50 mL) and placed into a Parr reactor (80 mL) containing 3 g of catalyst comprising Ru (5 wt percent) on carbon. Hydrogenation is carried out at 1,000 psi (6,895 kPa) hydrogen and at 100° C. The reaction is monitored by $^{31}P$ and $^1H$ NMR. After 2 weeks, resonances for the aromatic protons in the $^1H$ NMR spectrum disappear, and new resonances appear in the $^{31}P$ NMR spectrum. The mixture is filtered; a black solid on the filter is washed with methanol. The solvent is evaporated, and the residue is dried in vacuum to give a white solid identified as sodium 3-(dicyclohexylphosphinyl)cyclohexane-1-sulfonate (DCHPOCHS-Na). Yield 2.54 g (83%). $^{31}P\{^1H\}$ NMR ($CD_3OD$, ppm): 5.68 (major, ca. 87%) and 57.99 (minor, ca. 13%).

(3) Preparation of Ethyl 3-(dicyclohexylphosphinyl)cyclohexane-1-sulfonate

Hydrochloric acid (0.7 g; 38 wt. % solution) is added to DCHPOCHS-Na (1.5 g; 3.8 mmoL) in ethanol (20 mL), and the mixture is stirred for 30 minutes. Then, the ethanol is evaporated, and the residue is dried in vacuum. Dichloromethane (20 mL) and triethylorthoacetate (1.85 g; 11.4 mmoL) are added to the residue, and the resulting mixture is stirred under reflux for 10 hours. The mixture is then washed with saturated sodium bicarbonate (15 mL), then water, and then dried with sodium sulfate. The organic solvent and excess reagent are removed. The residue obtained therefrom is dried in vacuum for 1 hour to yield Ethyl 3-(dicyclohexylphosphinyl)-cyclohexane-1-sulfonate (DCHPOCHS-Et). Yield: 1.36 g (89%) $^{31}P\{^1H\}$ NMR($C_6D_6$, ppm): 51.28 (major) and 49.24 (minor).

(4) Preparation of Ethyl 3-(dicyclohexylphosphino)cyclohexane-1-sulfonate

DCHPOCHS-Et (1.0 g; 2.47 mmoL) is dissolved in benzene (25 mL) and triethylamine (1.6 mL; 11.6 mmoL), and the resulting solution is placed into a 250 mL three-neck flask under nitrogen and cooled to 0° C. Trichlorosilane (1.3 mL; 12.6 mmoL) dissolved in benzene (5 mL) is slowly added to the solution. The mixture is warmed to room temperature and then refluxed for 1.5 hours. The solution turns yellow with a precipitate. $^{31}P$ NMR indicates that reduction of the phosphorus atom from valence V to III is complete. The mixture is quenched with oxygen-free water (40 mL) at 0° C., and triethylamine (15 mL) is added to pH 9-10. The water layer is extracted with benzene (40 mL). Combined organic phases are filtered, and the filtrate is dried with sodium sulfate. The benzene solvent is evaporated, and the residue is dried in vacuum to give 0.80 g (83%) of oil identified as ethyl 3-(dicyclohexylphosphino)cyclohexane-1-sulfonate, DCHPCHS-Et. $^{31}P\{^1H\}$ NMR($C_6D_6$, ppm): 10.76 (major) and 11.49 (minor); $^1H$ NMR($C_6D_6$, ppm): 0.89 (t, J=7 Hz, 3H, $CH_3$), 1.0-2.8 (m, 32H, cyclohexyl), 3.89 (q, J=7 Hz, 3H, $CH_2$).

(5) Preparation of 3-(Dicyclohexylphosphine)cyclohexane-1-sulfonic acid

DCHPCHS-Et (0.75 g; 1.93 mmoL) is placed in a flask containing sulfuric acid (0.227 g; 2.32 mmoL) in water (4 mL) and THF (9 mL), and the resulting mixture is stirred under nitrogen overnight. THF is removed in vacuum. A residue is extracted with methylene chloride (15 mL) twice and then dried over sodium sulfate. Solvent is evaporated under rotary vacuum. The residue is dried in vacuum for 1 hour to give 0.29 g (42%) 3-(Dicyclohexylphosphine)-cyclohexane-1-sulfonic acid, DCHPCHSH. $^{31}P\{^1H\}$ NMR ($CH_2Cl_2$, ppm): 28.65 (major) and 26.42 (minor).

(6) Preparation of Sodium Salt of 3-(Dicyclohexylphosphino)cyclohexane-1-sulfonic acid (Ligand 1)

DCHPCHSH (170 mg; 0.472 mmoL) is mixed under nitrogen with sodium hydroxide (18.9 mg; 0.472 mmoL) in methanol (5 mL). The solution is filtered; methanol is evaporated; and the solid residue is dried in vacuum for 1 hour. Yield of sodium 3-(dicyclohexylphosphino)-cyclohexane-1-sulfonic acid, DCHPCHS-Na, 90 mg (50%); pH for a 5% water solution is about 10. $^{31}P\{^1H\}$ NMR ($CD_3OD$, ppm): 12.30 (major) and 11.63 (minor). $^1H$ NMR ($CD_3OD$, ppm): 0.9-2.8 (m, 31H, cyclohexyls), 3.40-3.50 (m, 1H, H—C—$SO_3Na$). Electrospray MS: m/z 360 (MH$^+$).

Example 2

Figure 2:
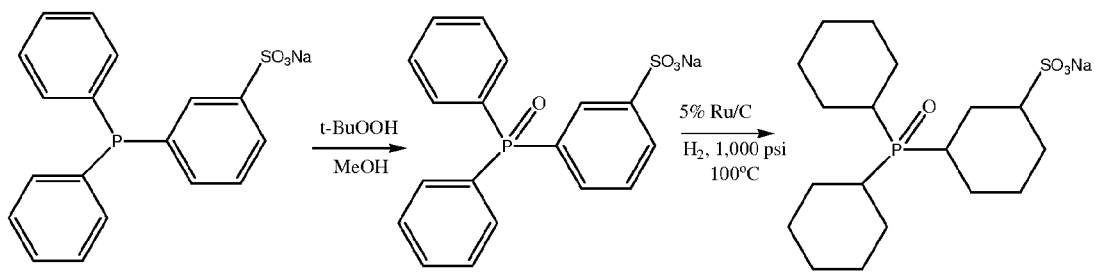
FIG. 2 illustrates the use of commercially available sodium 3-(diphenylphosphino)benzenesulfonate as a starting material for preparing the intermediate sodium 3-(dicyclohexylphosphinyl)cyclohexane-1-sulfonate.

Alternative Preparation of an Intermediate for Ligand 1 (with Reference to FIG. 2)

(1) Preparation of Sodium 3-(Diphenylphosphinyl)benzenesulfonate

Sodium 3-(diphenylphosphino)benzenesulfate is commercially available from TCI America Organic Chemicals or Strem Chemicals Inc, The commercial material (27.3 g; 75 mmoL) is dissolved in methanol (250 mL) and stirred for 3 hours at room temperature with slowly added tert-butyl hydroperoxide (11.6 ml of 70 wt % solution in water; 84 mmoL). Reaction completion is established by HPLC. The solvent is removed on a rotary evaporator, and the residue is washed twice with hexane (25 mL) and then dried in vacuum to yield sodium 3-(diphenylphosphinyl)benzenesulfonate (DPPOBS-Na). Yield 28.2 g (99%). $^{31}$P{$^1$H} NMR (CH$_3$OD, ppm): 33.44.

(2) Preparation of Sodium 3-(dicyclohexylphosphinyl)cyclohexane-1-sulfonate

DPPOBS-Na (7.0 g; 18.4 mmoL), prepared as above, is dissolved in dry methanol (70 mL) and placed into a Parr reactor (150 mL) containing 7 g of catalyst comprising Ru (5 wt percent) on carbon. Hydrogenation is carried out at 1,000 psi (6,895 kPa) hydrogen and at 100° C. The reaction is monitored by $^{31}$P and $^1$H NMR. After 2 weeks, resonances for the aromatic protons in the $^1$H NMR spectrum disappear, and new resonances appear in the $^{31}$P NMR spectrum. The mixture is filtered; a black solid on the filter is washed with methanol. The solvent is evaporated, and the residue is dried in vacuum to give a white solid identified as sodium 3-(dicyclohexylphosphinyl)cyclohexane-1-sulfonate (DCH-POCHS-Na). Yield 4.0 g (55%). $^{31}$P{$^1$H} NMR (CD$_3$OD, ppm): 5.68 (major, ca. 87%) and 57.99 (minor, ca. 13%). (3) Step 3 of Example 1 is repeated using the intermediate product from step (2) of this example. Subsequently, steps 4 to 6 of Example 1 are also reproduced to yield Ligand 1 of this invention, namely, the sodium salt of 3-(dicyclohexylphosphino)cyclohexane-1-sulfonic acid.

Example 3

Preparation of Ligand 4

(1) Preparation of dicyclohexylphosphine-borane solution

Dicyclohexyl phosphine (49.6 g, 0.25 moles) and 250 ml of dry THF are placed under nitrogen in a dry one-liter four-neck flask equipped with a thermometer, mechanical stirrer, reflux condenser, pressure-equalized dropping funnel, and nitrogen inlet. The solution is cooled to 0° C. and 250 ml of a 0.1 M solution of borane in THF is added dropwise. The colorless solution is stirred briefly at 0° C. and then at room temperature for 1 hour.

(2) Preparation of lithium 3-(dicyclohexylphosphino)butane-1-sulfonate-borane The solution from (1) is cooled to −60° C. and n-butyl lithium in hexane (164 ml of 1.6 normal solution, 0.262 moles) is added dropwise. After the end of the addition, the mixture is allowed to warm up to room temperature and stirred for 2 more hours. 3-Methyl-1,3-propane sultone (35.7 g, 0.262 moles) is dissolved in dry THF (40 ml) and the obtained solution is added dropwise at 0° C. to the reaction mixture above. After the end of addition, the mixture is stirred at room temperature for 1 hour, sampled for $^{31}$P NMR, and allowed to stand overnight.

(3) Preparation of lithium 3-(dicyclohexylphosphino)butane-1-sulfonate

The reaction mixture from (2) is evaporated to dryness under vacuum. The oily residue is dissolved in morpholine (300 ml) at 110° C. and stirred overnight. After cooling to room temperature, the product crystallizes. The crystals are filtered off in the nitrogen box, washed with nitrogen-sparged acetone, and thoroughly dried in a Kugelrohr distillation apparatus under vacuum and 120° C. Such thorough drying removes any residual morpholine and/or morpholine-borane contaminants adsorbed on the isolated solid product. $^{31}$P{$^1$H} NMR (CD$_3$OD, ppm): −3.45. $^1$H NMR (CD$_3$OD, ppm): 1.1-1.85 (m, 25H, cyclohexyls+CHCH$_2$), 1.30 (d, J=6.6 Hz, 3H, CH$_3$), 3.72 (m, 2H, CH$_2$SO$_3$Na). $^{13}$C NMR (CD$_3$OD, ppm): 13.94 (CH$_3$), 18.14, 18.35 (CH), 25.02 (CH$_2$), 26.8-33.2 (cyclohexyls), 56.36, 56.53 (CH$_2$SO$_3$Li).

What is claimed is:

1. A composition comprising a sulfonated triorganophosphine compound represented by the following formula:

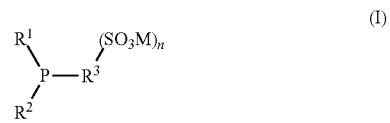

wherein $R^1$ and $R^2$ each individually represent a monovalent hydrocarbyl or substituted hydrocarbyl radical selected from alkyl, aralkyl, and alicyclic radicals; wherein $R^3$ represents a divalent or polyvalent alicyclic radical, which is bonded to the phosphorus atom and to one or more sulfonate substituents; further wherein $R^3$ does not contain any aryl moieties; wherein M comprises a monovalent cation, and n is an integer from 1 to 3 representing a total number of sulfonate substituents; and further wherein in each of $R^1$, $R^2$, and $R^3$ a carbon atom attached to the phosphorus atom or a carbon atom directly bonded to a carbon atom attached to the phosphorus atom is additionally bonded to at least 2 other carbon atoms.

2. The composition of claim 1 wherein $R^1$ and $R^2$ are each individually selected from alkyl radicals containing from 3 to 12 carbon atoms, aralkyl radicals containing from 6 to 12 carbon atoms, and alicyclic radicals containing from 3 to 10 carbon atoms.

3. The composition of claim 1 wherein $R^1$ and $R^2$ are each individually selected from iso-propyl, iso-butyl, sec-butyl, tert-butyl, 2,2-dimethylpropyl, 2-methylbutyl, 1,1-dimethylpropyl, 2-ethylhexyl, benzyl, 2-methylbenzyl, 2,6-dimethylbenzyl, 1-phenylethyl, phenylcyclohexyl, 1,2,3,4-tetrahydronaphthyl, phenylcyclopentyl, cyclopentyl, cyclohexyl, cycloheptyl, cyclooctyl, ethylcyclohexyl, norbornyl, adamantyl, and dicyclopentyl.

4. The composition of claim 1 wherein $R^1$ and $R^2$ are substituted with one or more substituents selected from cyano, fluoro, trifluoromethyl, trialkylsilyl, alkoxy, carboalkoxy (ester), dialkylamino, and dialkylamido.

5. A complex catalyst or complex catalyst precursor composition comprising a Group 8, 9, or 10 transition metal bonded to at least one ligand represented by the composition of claim 1, the transition metal optionally being further bonded to carbon monoxide, hydrogen, or both carbon monoxide and hydrogen.

6. The complex catalyst of claim 5 wherein the transition metal is selected from ruthenium, rhodium, cobalt, and iridium.

7. A complex catalyst solution or complex catalyst precursor solution comprising a solvent, a complex catalyst or catalyst precursor composition comprising a Group 8, 9, or 10 transition metal bonded to at least one ligand, the solution optionally further comprising free ligand; wherein the bonded and free ligands are represented by the composition of claim 1; and wherein optionally the Group 8, 9, or 10 transition metal can be further bonded to carbon monoxide, hydrogen, or both carbon monoxide and hydrogen.

8. A hydroformylation process comprising contacting one or more olefinically-unsaturated compounds with carbon monoxide and hydrogen in the presence of a transition metal-ligand complex catalyst, and optionally free ligand, wherein the ligand is represented by the composition of claim 1, the contacting being conducted under process conditions sufficient to prepare one or more corresponding aldehyde products.

9. The process of claim 8 wherein the olefin is selected from olefinically-unsaturated aliphatic hydrocarbons having from 10 to 50 carbon atoms.

10. The process of claim 8 wherein the olefin is selected from the group consisting of alpha olefins, internal olefins, alkyl alkenoates, alkenyl alkanoates, alkenyl alkyl ethers, alkenols, olefinically-unsaturated fatty acids, and olefinically-unsaturated fatty acid esters.

11. The process of claim 8 wherein the Group 8, 9, or transition metal is present in a concentration greater than 0 parts per million (ppm) and less than 1,000 ppm by weight, calculated as free metal.

12. The process of claim 8 wherein temperature is greater than 30° C. and less than 150° C.

13. The process of claim 8 wherein total gas pressure of hydrogen, carbon monoxide, and the olefinic unsaturated reactant in the hydroformylation process ranges from greater than 1 psia (7 kPa) to less than 10,000 psia (68,948 kPa).

14. The process of claim 8 wherein partial pressure of carbon monoxide is greater than 1 psia (7 kPa) and less than 1000 psia (6,8948 kPa), and wherein partial pressure of hydrogen is greater than 5 psia (35 psia) and less than 1000 psia (6,8948 kPa).

15. The process of claim 8 wherein a molar ratio $H_2/CO$ of gaseous hydrogen to carbon monoxide is greater than 1/10 and less than 100/1.

16. The process of claim 8 wherein the transition metal is selected from ruthenium, rhodium, cobalt, and iridium.

17. The composition of claim 1 wherein $R^3$ is selected from the following radicals:

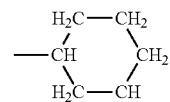

II

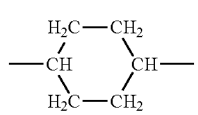

III

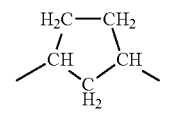

IV

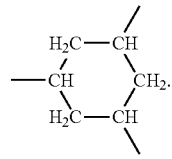

V

18. The composition of claim 1 selected from compounds of the following formula:

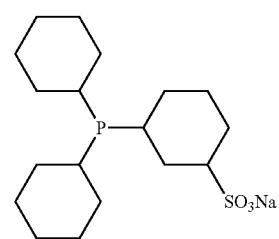

Ligand 1

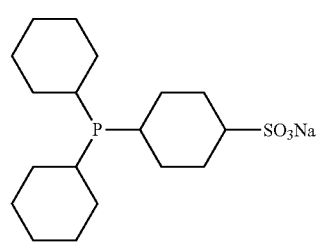

Ligand 2

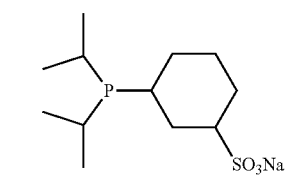

Ligand 3

Ligand 4

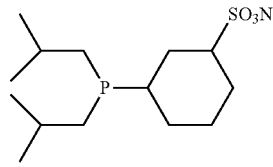

Ligand 5

* * * * *